(12) United States Patent
Donaldson et al.

(10) Patent No.: US 10,881,530 B2
(45) Date of Patent: Jan. 5, 2021

(54) SURGICAL INSTRUMENT AND METHOD

(71) Applicant: Warsaw Orthopedic, Inc, Warsaw, IN (US)

(72) Inventors: Cathlene Donaldson, Memphis, TN (US); Jesse W. Peters, Merritt Island, FL (US); Jerald L. Redmond, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 286 days.

(21) Appl. No.: 15/582,142

(22) Filed: Apr. 28, 2017

(65) Prior Publication Data

US 2018/0311051 A1 Nov. 1, 2018

(51) Int. Cl.
*A61F 2/46* (2006.01)
*A61B 34/20* (2016.01)
*A61B 90/00* (2016.01)

(52) U.S. Cl.
CPC ............ *A61F 2/4611* (2013.01); *A61B 34/20* (2016.02); *A61B 2034/2051* (2016.02); *A61B 2034/2055* (2016.02); *A61B 2090/376* (2016.02); *A61B 2090/3762* (2016.02); *A61B 2090/3983* (2016.02)

(58) Field of Classification Search
CPC .................................................. A61F 2/4611
USPC ................................ 606/99–100, 80, 81, 91
See application file for complete search history.

(56) References Cited

U.S. PATENT DOCUMENTS

| | | | |
|---|---|---|---|
| 6,021,343 A * | 2/2000 | Foley | A61B 17/16 600/417 |
| 6,711,431 B2 * | 3/2004 | Sarin | A61B 5/103 600/426 |
| 7,549,998 B2 | 6/2009 | Braun | |
| 7,976,549 B2 | 7/2011 | Dye et al. | |
| 8,771,282 B2 | 7/2014 | Blain et al. | |
| 8,864,829 B1 | 10/2014 | Bruffey et al. | |
| 8,998,924 B2 | 4/2015 | Simpson et al. | |
| 9,078,672 B1 * | 7/2015 | Rosse | A61B 17/1631 |
| 2002/0077540 A1 * | 6/2002 | Kienzle, III | A61B 17/1703 600/424 |
| 2004/0153080 A1 * | 8/2004 | Dong | A61B 17/1666 606/80 |
| 2005/0021043 A1 * | 1/2005 | Jansen | A61B 5/064 606/102 |
| 2005/0216022 A1 * | 9/2005 | Lechot | A61B 17/1631 606/81 |
| 2007/0233150 A1 * | 10/2007 | Blain | A61B 17/17 606/96 |
| 2007/0293869 A1 * | 12/2007 | Conte | A61B 17/1666 606/91 |
| 2008/0058804 A1 * | 3/2008 | Lechot | A61B 17/1631 606/53 |

(Continued)

*Primary Examiner* — Matthew J Lawson
(74) *Attorney, Agent, or Firm* — Sorell, Lenna & Schmidt, LLP (57) ABSTRACT

A surgical instrument comprises a member defining a longitudinal axis and is connectable with a spinal implant. The member is connected to a handle disposed transverse relative to the axis and rotatable about the axis. An image guide is connected with the member and oriented relative to a sensor to communicate a signal representative of a position of the spinal implant. Systems, implants, spinal constructs and methods are disclosed.

18 Claims, 8 Drawing Sheets

(56) References Cited

U.S. PATENT DOCUMENTS

| | | | | |
|---|---|---|---|---|
| 2012/0157887 A1* | 6/2012 | Fanson | ................... | A61F 2/46 |
| | | | | 600/595 |
| 2013/0261609 A1* | 10/2013 | Dicorleto | ........... | A61B 17/1622 |
| | | | | 606/1 |
| 2014/0142642 A1* | 5/2014 | Wallenstein | .......... | A61F 2/4465 |
| | | | | 606/86 A |
| 2016/0106551 A1* | 4/2016 | Grinnberg, Jr. | ....... | A61F 2/4455 |
| | | | | 623/17.16 |
| 2016/0143649 A1* | 5/2016 | Weekes | .............. | A61B 17/1622 |
| | | | | 606/80 |
| 2018/0085232 A1* | 3/2018 | Palmatier | .............. | A61F 2/4611 |

\* cited by examiner

SURGICAL INSTRUMENT AND METHOD

TECHNICAL FIELD

The present disclosure generally relates to medical devices for the treatment of musculoskeletal disorders, and more particularly to a surgical system and a method for treating a spine.

BACKGROUND

Spinal pathologies and disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, corpectomy, discectomy, laminectomy and implantable prosthetics. For example, fusion and fixation treatments may be performed that employ implants to restore the mechanical support function of vertebrae. Surgical instruments are employed, for example, to prepare tissue surfaces for disposal of the implants. Surgical instruments are also employed to engage implants for disposal with the tissue surfaces at a surgical site. This disclosure describes an improvement over these prior technologies.

SUMMARY

In one embodiment, a surgical instrument is provided. The surgical instrument comprises a member defining a longitudinal axis and is connectable with a spinal implant. The member is connected to a handle disposed transverse relative to the axis and rotatable about the axis. An image guide is connected with the member and oriented relative to a sensor to communicate a signal representative of a position of the spinal implant. The image guide is disposed in a fixed position with the member. In some embodiments, surgical systems, implants, spinal constructs and methods are provided.

In one embodiment, the surgical instrument comprises a shaft that defines a longitudinal axis and is connectable with a spinal implant. The shaft is connected to a handle disposed transverse relative to the axis and rotatable about the axis. An actuator is connected with the shaft and the handle and is disposable in a locked orientation and a non-locking orientation. An image guide is connected with the shaft and oriented relative to a sensor to communicate a signal representative of a position of the spinal implant. The image guide is disposed in a fixed position with the member.

In one embodiment, a surgical system is provided. The surgical system comprises an interbody implant. A surgical instrument is connectable with the interbody implant. The surgical instrument includes a member defining a longitudinal axis and a handle is disposed transverse relative to the axis and rotatable about the axis. An actuator is connected with the member and the handle and disposable in a locked orientation and a non-locking orientation. An image guide is connected with the member and oriented relative to a sensor to communicate a signal representative of a position of the interbody implant. The image guide is disposed in a fixed position with the member. A tracking device includes the sensor that receives the signal and communicates with a processor to generate data for display of an image from a monitor. The image represents a position of the interbody implant relative to tissue.

BRIEF DESCRIPTION OF THE DRAWINGS

The present disclosure will become more readily apparent from the specific description accompanied by the following drawings, in which.

DETAILED DESCRIPTION

The exemplary embodiments of a surgical system are discussed in terms of medical devices for the treatment of musculoskeletal disorders and more particularly, in terms of a surgical system for preparing a surgical site, and a method for treating a spine. In some embodiments, the surgical system includes a surgical instrument including a handle employed with an image guide oriented relative to a sensor to communicate a signal representative of a position of a spinal implant. In some embodiments, the surgical system includes a surgical navigation system.

In some embodiments, the present surgical system includes a surgical instrument comprising a navigated inserter handle. In some embodiments, the present surgical system includes a surgical instrument comprising a navigated inserter handle employed with an expandable interbody implant. In some embodiments, the present surgical system includes a surgical instrument including an auto-locking multiple position handle actuated by a rear button. For example, a practitioner engages a spring-loaded button and a pin travels forward within a slot. In some embodiments, the slot intersects a groove of similar size, allowing the handle to move and/or rotate in any direction. In some embodiments, the button is released and the spring force causes the pin to travel back into the nearest slot thereby locking the position of the handle relative to the surgical instrument.

In some embodiments, the present surgical system includes a surgical instrument comprising an interbody inserter for use with a surgical navigation system for placement of an expandable interbody device. In some embodiments, the inserter includes a rotatable handle that can be adjusted to reposition the handle relative to the interbody device and a navigation tracker. In some embodiments, rotation of the handle is actuated by engaging/pushing a spring-loaded button on the proximal end of the inserter such that an internal locking pin is disengaged from a locking slot on the inserter shaft. In some embodiments, the pin is translated and fully disengaged such that the handle is rotated relative to the inserter shaft to a desired position. In some embodiments, the button is releasable such that the locking pin snaps back into one of the plurality of locking slots, for example, four locking slots, to lock the handle position, which can enable use of the surgical instrument for a procedure.

In some embodiments, the present surgical system includes a surgical instrument employed with a method of using a navigation system in navigated spine procedures. In some embodiments, the surgical instrument can be employed with optical-based navigation systems to facilitate surgical instrument line of sight between an instrument tracker and a camera. In some embodiments, this configuration facilitates the ability to consistently track surgical instrument position throughout a surgical procedure in connection with location of a navigation camera in an operating room and for patient positioning. In some embodiments, the present surgical system includes a surgical instrument having a rotatable handle that allows a surgeon to be positioned on either side of a patient and adjust the handle position relative to a navigation tracker to accommodate operating room setup. In some embodiments, the present surgical system includes a surgical instrument having a four position configuration that provides adjustability of hand orientation relative to the patient for ergonomic placement of a spinal implant. In some embodiments, the surgical instrument includes a handle having an active unlock and passive lock actuation mechanism, which resists and/or prevents the potential for accidental movement of a surgical tracker during use.

In some embodiments, the surgical instrument includes an actuator having a button and a pin. In some embodiments, the pin is fully seated with a slot of a shaft in the locking orientation. In some embodiments, the pin translates into a groove into a non-locking orientation. In some embodiments, in the non-locking orientation, the handle is configured to rotate freely relative to the shaft.

In some embodiments, the present surgical system includes a surgical instrument that has an instrument tracker and a distal/working end. In some embodiments, the surgical tracker provides indicia and/or display of a location and angulation of the surgical instrument and its distal/working end. In some embodiments, the surgical system includes a surgical instrument having one or more image guides, which include one or more fiducial markers. In some embodiments, the fiducial marker includes a single ball-shaped marker. In some embodiments, the image guide is disposed adjacent a proximal end of the surgical instrument. In some embodiments, the image guide provides indicia and/or display of a precise rotational and/or linear position of the image guide on the surgical instrument. In some embodiments, this configuration provides indicia and/or display of an amount of manipulation, movement, translation and/or rotation of the implant with tissue.

In some embodiments, the surgical system includes a surgical instrument having one or more image guides, which include a tracker that provides location of a surgical instrument in three dimensions, and a tracker that provides location of the surgical instrument and/or a spinal implant in two dimensions, such as, for example, a selected plane. In some embodiments, this configuration provides indicia and/or display of implant position corresponding to an amount of manipulation, movement, translation and/or rotation of the implant with tissue.

In some embodiments, the surgical instrument includes a navigation tracker that is optically tracked and requires a line-of-sight view to a sensor, such as, for example, a camera. In some embodiments, the surgical system includes a navigation tracker attached to a surgical instrument and is disposed in a direct line of sight of a sensor, which includes one or more cameras. In some embodiments, the surgical system includes an O-arm medical imaging device that digitally captures images of an anatomy. In some embodiments, the tracker communicates with a surgical navigation system to determine and/or display surgical instrument positioning relative to the anatomy.

In some embodiments, one or all of the components of the surgical system may be disposable, peel pack and/or pre packed sterile devices. One or all of the components of the surgical system may be reusable. The surgical system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the surgical system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1-11, there are illustrated components of a surgical system 10.

The components of surgical system 10 can be fabricated from biologically acceptable materials suitable for medical applications, including metals, synthetic polymers and/or ceramics. For example, the components of surgical system 10, individually or collectively, can be fabricated from materials such as stainless steel alloys, aluminum, commercially pure titanium, titanium alloys, Grade 5 titanium, super-elastic titanium alloys, cobalt-chrome alloys, super-elastic metallic alloys (e.g., Nitinol, super elasto-plastic metals, such as GUM METAL®), ceramics, thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene and/or epoxy.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 is employed, for example, with a fully open surgical procedure, a minimally invasive procedure including percutaneous techniques, and mini-open surgical techniques to deliver and introduce instrumentation and/or one or more implants at a surgical site within a body of a patient, for example, a section of a spine. In some embodiments, surgical system 10 includes a surgical instrument having a multiple position handle for delivering and introducing a spinal implant, such as, for example, an interbody implant to the surgical site. In some embodiments, the surgical instrument allows a surgeon to be variably positioned about a patient and is adjustable relative to a navigation tracker to accommodate operating room setup, which can facilitate ergonomic placement of a spinal implant. In some embodiments, the surgical instrument can be configured to deliver and introduce one or more components of a spinal construct, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Figure 1:
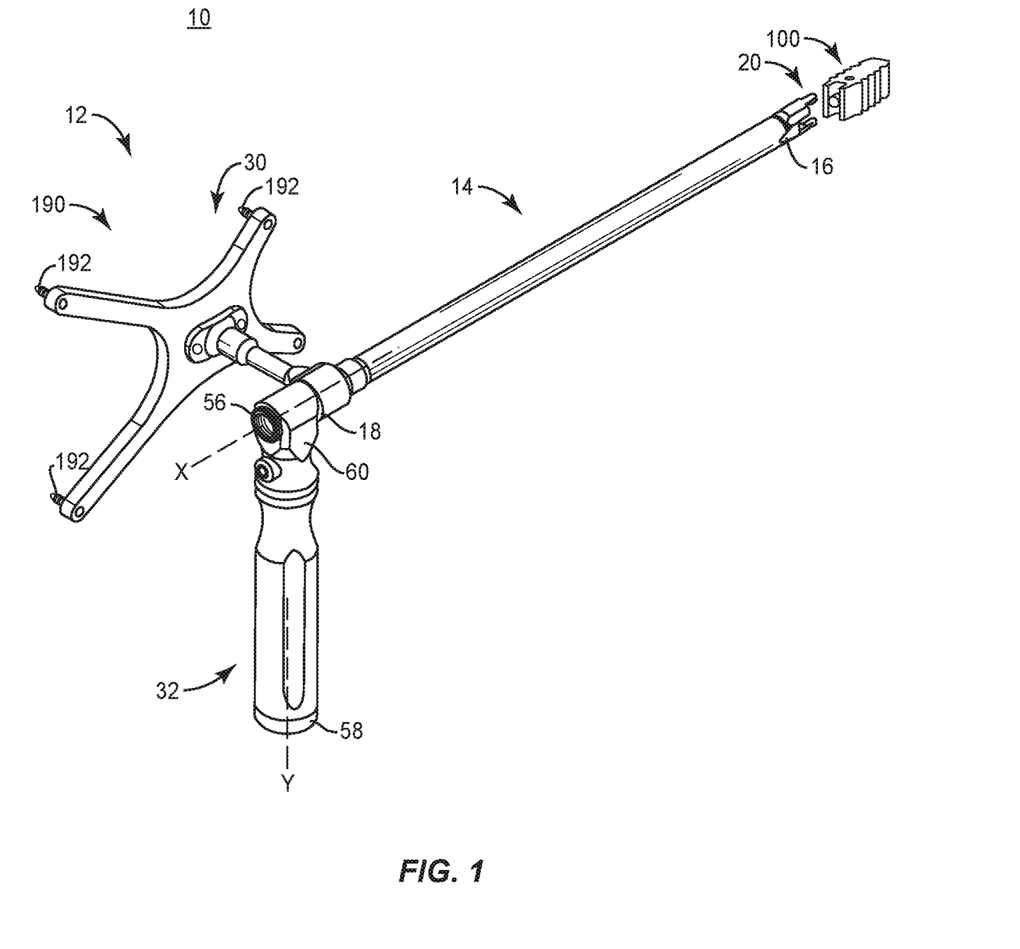
FIG. 1 is a perspective view of components of one embodiment of a surgical system in accordance with the principles of the present disclosure.
Figure 2:
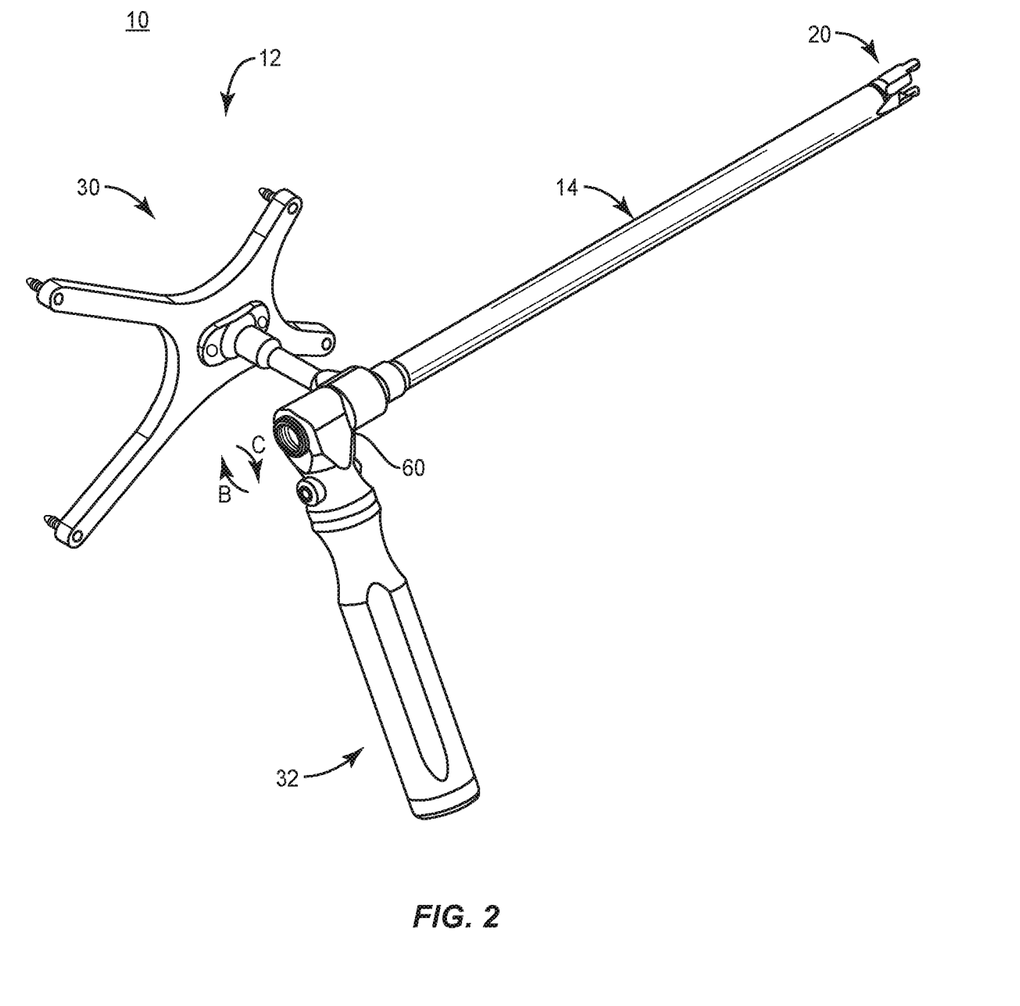
FIG. 2 is a perspective view of components of one embodiment of a surgical system in accordance with the principles of the present disclosure.
Figure 3:
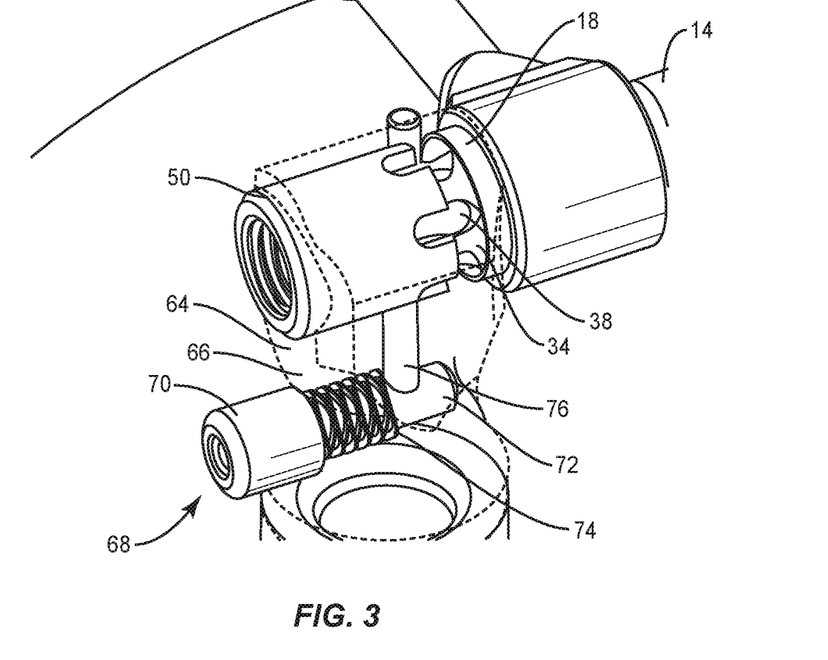
FIG. 3 is a break away view, in part phantom, of components of the surgical system shown in FIG. 1.
Figure 4:
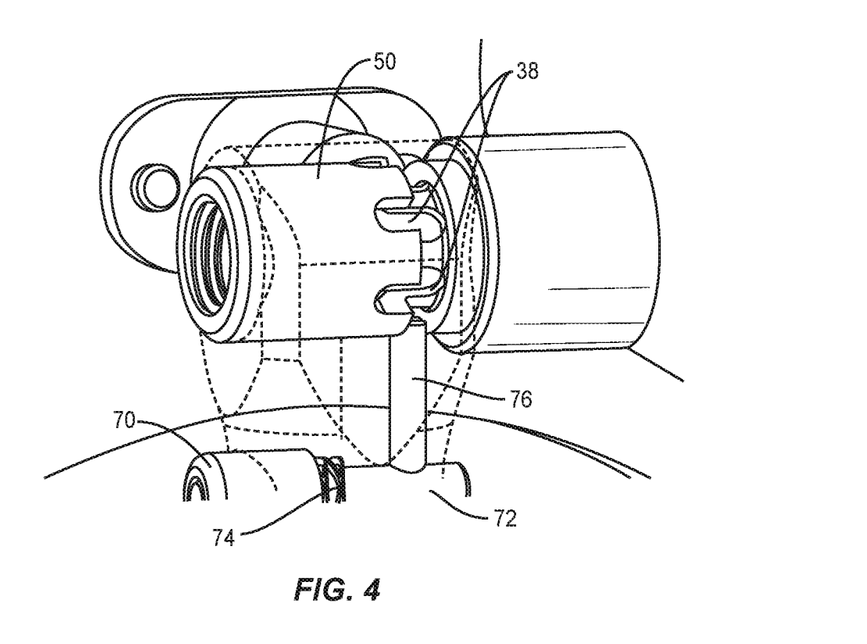
FIG. 4 is a break away view, in part phantom, of components of the surgical system shown in FIG. 1.
Figure 5:
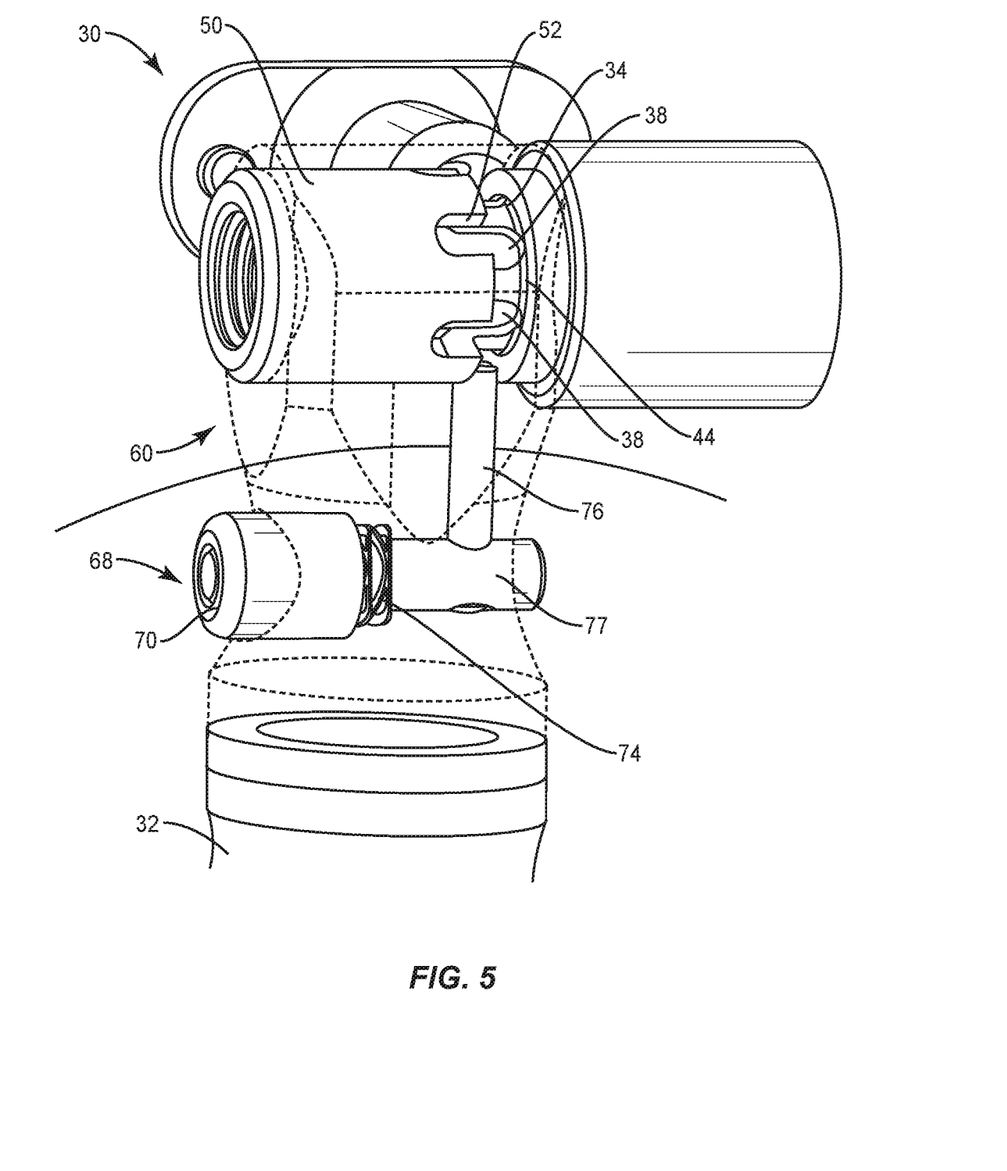
FIG. 5 is an enlarged view of the components of the surgical system shown in FIG. 4.

Surgical system 10 includes a surgical instrument, such as, for example, an inserter 12. Inserter 12 includes a member, such as, for example, a shaft 14. Shaft 14 extends between an end 16 and an end 18 and defines a longitudinal axis X. End 16 includes an engagement portion 20 configured for engagement with an interbody implant 100, as described herein. End 18 is connected with an image guide, such as, for example, a navigation component 30, as described herein. End 18 is connected with a handle 32, as described herein. Navigation component 30 is fixed with end 18 such that navigation component 30 remains stationary upon rotation of a handle 32 relative to shaft 14, as shown in FIG. 2 and described herein. Navigation component 30 is fixed with end 18 at a selected distance from one or more components of inserter 12 and/or a spinal implant connected with inserter 12 to represent position and/or orientation of one or more components of inserter 12, a spinal implant and/or tissue, as described herein.

Figure 8:
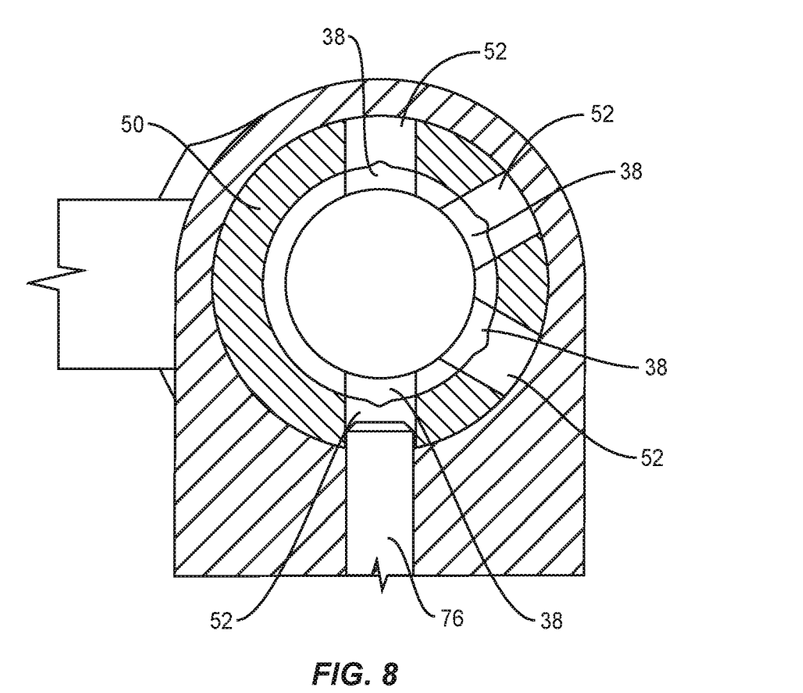
FIG. 8 is a cross section view of the components of the system shown in FIG. 1.

End 18 includes an inner shaft 34 extending therefrom. Shaft 34 includes a surface 36 that defines a plurality of slots 38. Slots 38 are spaced apart and circumferentially disposed about shaft 34 in a semi-circular configuration. In some embodiments, shaft 34 includes four, equidistantly spaced apart slots 38 disposed in a semi-circular configuration, as shown in FIG. 8. In some embodiments, surface 36 may include alternate surface configurations, such as, for example, rough, arcuate, undulating, mesh, porous, semi-porous, dimpled and/or textured. Surface 36 defines a groove 44 disposed circumferentially about shaft 34. A portion of an actuator 68, such as, for example, a pin 76 is configured to freely translate within groove 44 during rotation of handle 32 for selective positioning of handle 32 relative to shaft 14, as described herein.

Shaft 34 includes a collar 50. Collar 50 includes slots 52 spaced apart and circumferentially disposed about collar 50 in a semi-circular configuration. Slots 52 are disposed such that pin 76 is movable from groove 44 into slots 52 for capture in a locked orientation by collar 50, as described herein. Slots 52 are configured to provide a plurality of selected positions for positioning handle 32 relative to shaft 14. In some embodiments, shaft 34 includes four, equidistantly spaced apart slots 52 disposed in a semi-circular configuration, as shown in FIG. 8. This configuration provides four alternate locking positions of handle 32 relative to shaft 14. In some embodiments, slots 52 are disposed in communication and alignment with slots 38.

Handle 32 includes an end 56 and an end 58, and defines an axis Y. Handle 32 extends between ends 56, 58 transverse to shaft 14. In some embodiments, handle 32 may be disposed at alternate orientations relative to shaft 14, such as, for example, parallel, perpendicular and/or other angular orientations such as acute or obtuse, co-axial, offset, and/or staggered. In some embodiments, handle 32 may include alternate surface configurations to enhance gripping of handle 32, such as, for example, rough, arcuate, undulating, mesh, porous, semi-porous, dimpled and/or textured. In some embodiments, handle 32 may include alternate cross section configurations, such as, for example, oval, oblong, triangular, square, hexagonal, polygonal, irregular, uniform, non-uniform and/or tapered.

Figure 6:
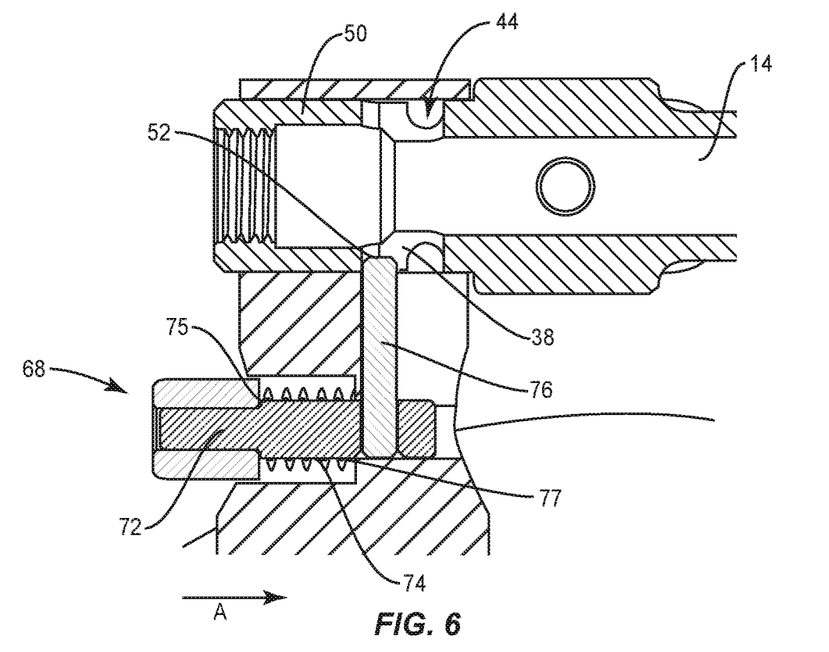
FIG. 6 is a cross section view of the components of the surgical system shown in FIG. 4.
Figure 7:
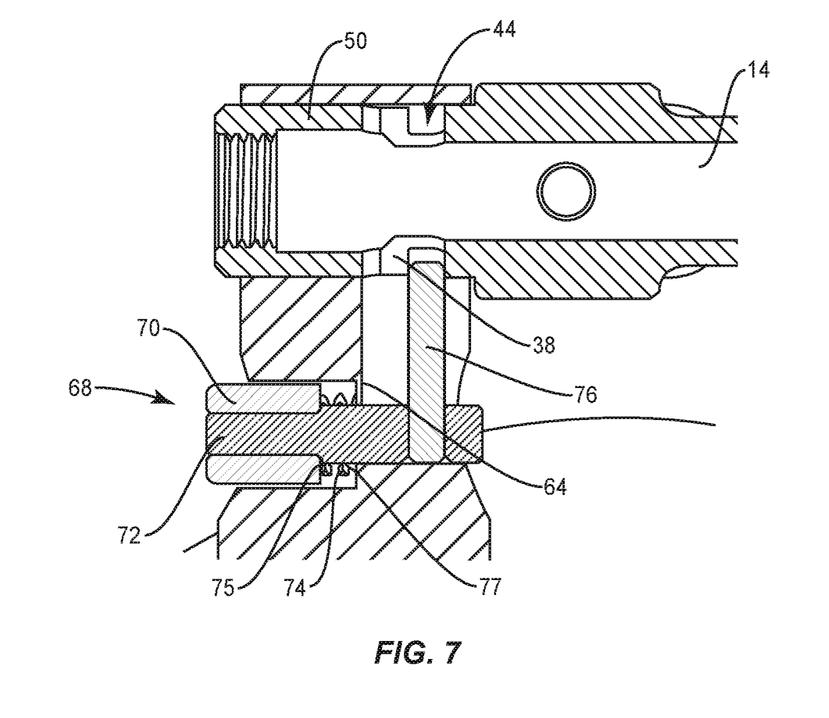
FIG. 7 is a cross section view of the components of the surgical system shown in FIG. 4.
Figure 9:
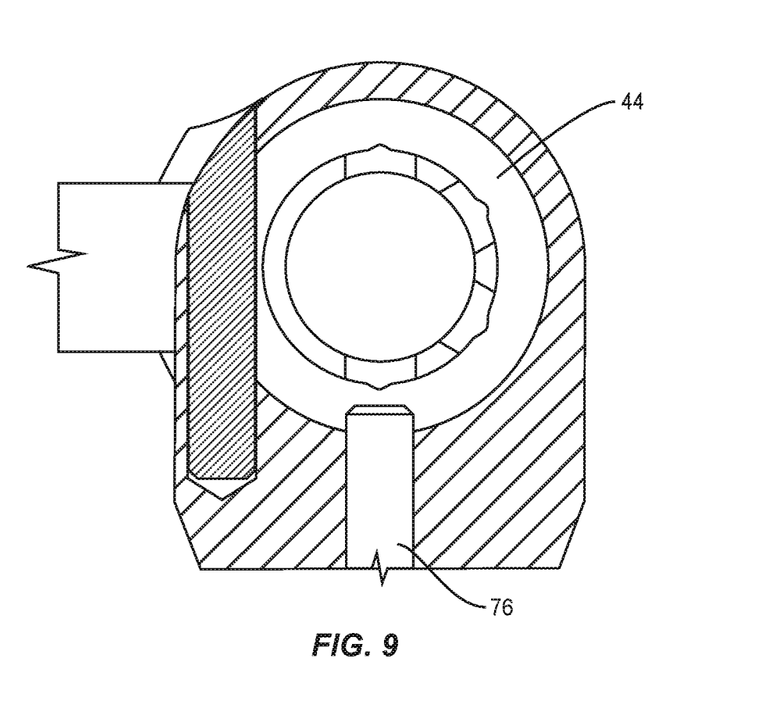
FIG. 9 is a cross section view of the components of the system shown in FIG. 1.
Figure 10:
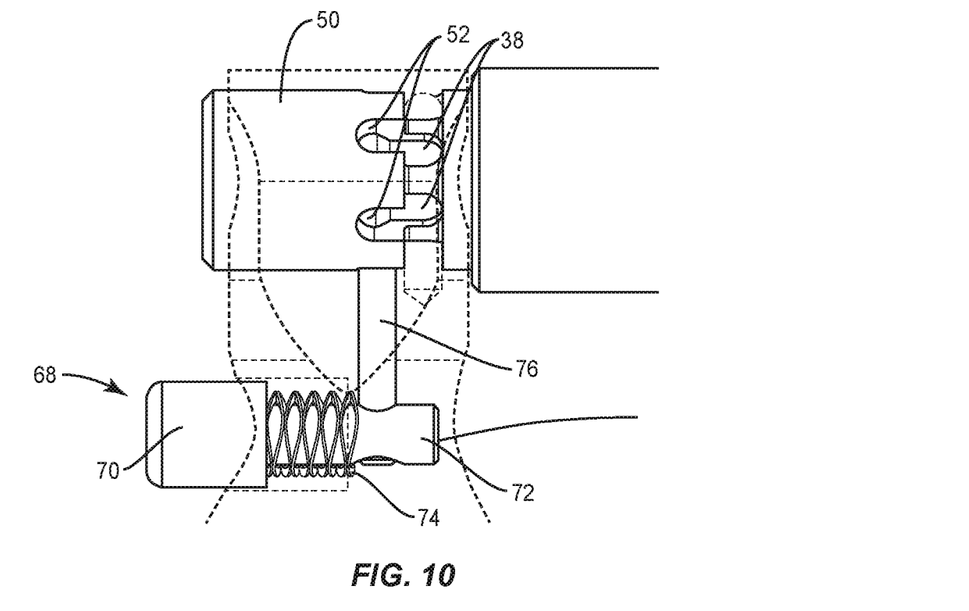
FIG. 10 is a side view, in part phantom, of components of the surgical system shown in FIG. 1.
Figure 11:
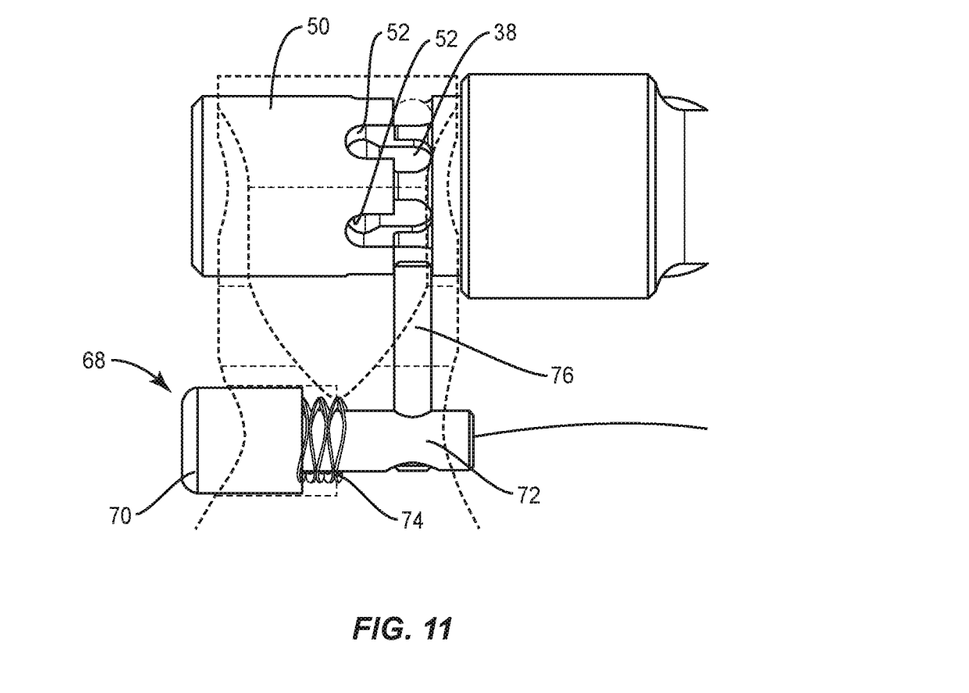
FIG. 11 is a side view, in part phantom, of components of the surgical system shown in FIG. 1.

End 56 includes a housing 60 having a surface 64 that defines a cavity 66. Cavity 66 is configured for disposal of end 18 of shaft 14 and actuator 68, as described herein. Actuator 68 is moveable between a locked orientation, as shown in FIGS. 6 and 8, and a non-locking orientation, as shown in FIGS. 7 and 9. Actuator 68 includes a button 70. Button 70 is connected with a shaft 72. Shaft 72 extends parallel to axis X. In some embodiments, shaft 72 may be disposed at alternate orientations relative to axis X, such as, for example, perpendicular and/or other angular orientations such as acute or obtuse, co-axial, offset, and/or staggered.

A spring 74 is disposed about shaft 74 and within cavity 66. Spring 74 extends between an end 75 and an end 77. End 75 is engaged with a surface of button 70 and end 77 is engaged with surface 64. When spring 74 is disposed in an expanded position, spring 74 applies a force to button 70 such that button 70 is resiliently biased into the locked orientation, as shown in FIGS. 6 and 8. As such, button 70 is spring loaded into the locked orientation. When a force is applied to button 70, for example via manual engagement, the force overcomes the force applied by spring 74 causing button 70 to translate shaft 72 into the non-locking orientation, as shown in FIGS. 7 and 9.

Shaft 72 includes pin 76, which extends transversely therefrom. In some embodiments, pin 76 extends perpendicular to shaft 72. In some embodiments, pin 76 may be disposed at alternate orientations relative to shaft 74, such as, for example, parallel, and/or other angular orientations such as acute or obtuse, co-axial, offset, and/or staggered. Pin 76 extends from shaft 72 for disposal with one of slots 52, as shown in FIGS. 6, 8 and as described herein. Actuation of button 70 is configured to disengage pin 76 from one of slots 52 into groove 44 to facilitate unrestricted rotation of handle 32, as described herein.

For example, a force applied to button 70 overcomes the force applied by spring 74 on button 70 causing shaft 72 to translate, in a direction shown by arrow A in FIG. 6. In some embodiments, actuator 68 comprises a passive lock biased to the locked orientation such that spring 74 biases button 70, as described herein, to the locked orientation, as shown in FIGS. 6 and 8.

Button 70 is engageable such that translation of shaft 72 causes pin 76 to disengage and/or be translated from slots 52. In some embodiments, actuator 68 comprises an active unlocking configuration for disposal of pin 76 in groove 44 and free rotation of handle 32 relative to shaft 14, such that button 70 is engageable to overcome the bias of spring 74 and disposal of button 70 in the non-locking orientation, as shown in FIGS. 7 and 9. Pin 76 translates from slot 52 of collar 50 into groove 44. Handle 32 is freely rotatable, in the directions shown by arrows B and C in FIG. 2, to selectively orient handle 32 relative to shaft 14. Rotation of handle 32 causes pin 76 to translate within groove 44 for selective positioning of handle 32 relative to shaft 14.

Upon selective positioning of handle 32 relative to shaft 14, actuator 68 is released. Button 70 is resiliently biased into the locking orientation by spring 74 in the passive locking configuration. Button 70 is released and pin 76 translates from groove 44 to an adjacent slot 52 for capture of pin 76 with collar 50. In some embodiments, due to the relative positioning and/or orientation of pin 76 and slots 52 in the selected position of handle 32 relative to shaft 14, handle 32 can be manipulated, slightly, passively and/or incrementally to align pin 76 with the adjacent slot 52. Rotation of handle 32 facilitates adjustment of a position of handle 32 with inserter 12 to accommodate operating room setup while maintaining a position of navigation component 30. Rotation of handle 32 provides adjustability of hand orientation relative to the patient for ergonomic placement of interbody implant 100, as described herein.

Navigation component 30 is connected with shaft 14. Inserter 12 is configured for disposal adjacent a surgical site such that navigation component 30 is oriented relative to a sensor array 202 to facilitate communication between navigation component 30 and sensor array 202 during a surgical procedure, as described herein. Navigation component 30 is configured to generate a signal representative of a position of interbody implant 100 relative to inserter 12 and/or tissue. In some embodiments, the image guide may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals. In some embodiments, navigation component 30 is connected with shaft 14 via an integral connection, friction fit, pressure fit, interlocking engagement, mating engagement, dovetail connection, clips, barbs, tongue in groove, threaded, magnetic, key/keyslot and/or drill chuck.

Figure 12:
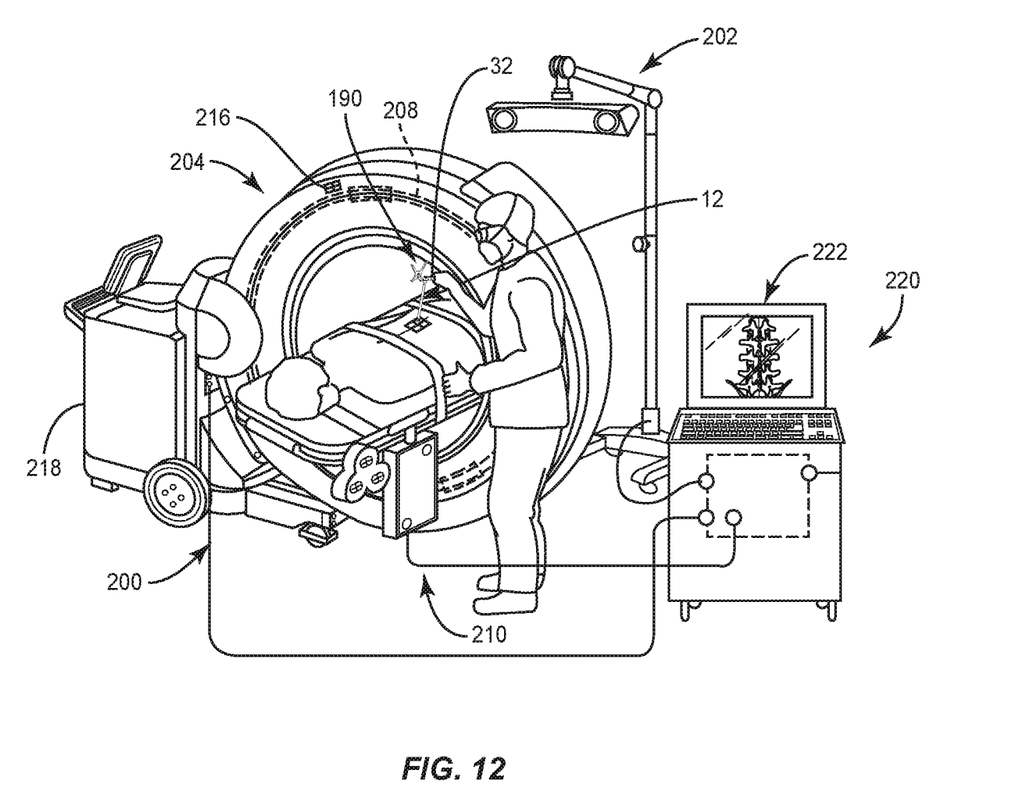
FIG. 12 is a perspective view of components one embodiment of a surgical system in accordance with the principles of the present disclosure.

Navigation component 30 includes an emitter array 190. Emitter array 190 is configured for generating a signal to sensor array 202 of a surgical navigation system 200, as shown in FIG. 12 and described herein. In some embodiments, the signal generated by emitter array 190 represents a position of interbody implant 100 relative to inserter 12 and relative to tissue, such as, for example, bone. In some embodiments, the signal generated by emitter array 190 represents a three dimensional position of interbody implant 100 relative to tissue.

In some embodiments, sensor array 202 receives signals from emitter array 190 to provide a three-dimensional spatial position and/or a trajectory of interbody implant 100 relative to inserter 12 and/or tissue. Emitter array 190 communicates with a processor of computer 220 of navigation system 200 to generate data for display of an image on monitor 222, as described herein. In some embodiments, sensor array 202 receives signals from emitter array 190 to provide a visual representation of a position of interbody implant 100 relative to inserter 12 and/or tissue. See, for example, similar surgical navigation components and their use as described in U.S. Pat. Nos. 6,021,343, 6,725,080, 6,796,988, the entire contents of each of these references being incorporated by reference herein.

Surgical navigation system 200 is configured for acquiring and displaying medical imaging, such as, for example, x-ray images appropriate for a given surgical procedure. In some embodiments, pre-acquired images of a patient are collected. In some embodiments, surgical navigation system 200 can include an O-arm® imaging device 204 sold by Medtronic Navigation, Inc. having a place of business in Louisville, Colo., USA. Imaging device 204 may have a generally annular gantry housing that encloses an image capturing portion 208.

In some embodiments, navigation system 200 comprises an image capturing portion 208 that may include an x-ray source or emission portion and an x-ray receiving or image receiving portion located generally or as practically possible 180 degrees from each other and mounted on a rotor (not shown) relative to a track of image capturing portion 208. Image capturing portion 208 can be operable to rotate 360 degrees during image acquisition. Image capturing portion 208 may rotate around a central point or axis, allowing image data of the patient to be acquired from multiple directions or in multiple planes. Surgical navigation system 200 can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, surgical navigation system 200 can include C-arm fluoroscopic imaging systems, which can generate three-dimensional views of a patient. The position of image capturing portion 208 can be precisely known relative to any other portion of an imaging device 204 of navigation system 200. In some embodiments, a precise knowledge of the position of image capturing portion 208 can be used in conjunction with a tracking system 210 to determine the position of image capturing portion 208 and the image data relative to the patient.

Tracking system 210 can include various portions that are associated or included with surgical navigation system 200. In some embodiments, tracking system 210 can also include a plurality of types of tracking systems, such as, for example, an optical tracking system that includes an optical localizer, such as, for example, sensor array 202 and/or an EM tracking system that can include an EM localizer. Various tracking devices can be tracked with tracking system 210 and the information can be used by surgical navigation system 200 to allow for a display of a position of an item, such as, for example, a patient tracking device, an imaging device tracking device 216, and an instrument tracking device, such as, for example, emitter array 190, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted to a computer 218 where they may be forwarded to computer 220. Image transfer may be performed over a standard video connection or a digital link including wired and wireless. Computer 220 provides the ability to display, via monitor 222, as well as save, digitally manipulate, or print a hard copy of the received images. In some embodiments, images may also be displayed to the surgeon through a heads-up display.

In some embodiments, surgical navigation system 200 provides for real-time tracking of the position of interbody implant 100 relative to inserter 12 and/or tissue can be tracked. Sensor array 202 is located in such a manner to provide a clear line of sight with emitter array 190, as described herein. In some embodiments, fiducial markers 192 of emitter array 190 communicate with sensor array 202 via infrared technology. Sensor array 202 is coupled to computer 220, which may be programmed with software modules that analyze signals transmitted by sensor array 202 to determine the position of each object in a detector space.

In assembly, operation and use, surgical system 10, similar to the systems and methods described herein, is employed with a surgical procedure for treatment of a spinal disorder affecting a section of a spine of a patient, as discussed herein. For example, the components of surgical system 10 can be used with a surgical procedure for treatment of a condition or injury of an affected section of the spine including vertebrae, as shown in FIG. 12. In some embodiments, one or all of the components of surgical system 10 can be delivered or implanted as a pre-assembled device or can be assembled in situ. Surgical system 10 may be completely or partially revised, removed or replaced.

The components of surgical system 10 can be employed with a surgical treatment of an applicable condition or injury of an affected section of a spinal column and adjacent areas within a body, such as, for example, vertebrae. In some embodiments, the components of surgical system 10 may be employed with one or a plurality of vertebra. To treat a selected section of vertebrae V, a medical practitioner obtains access to a surgical site including vertebrae in any appropriate manner, such as through incision and retraction of tissues. In some embodiments, the components of surgical system 10 can be used in any existing surgical method or technique including open surgery, mini-open surgery, minimally invasive surgery and percutaneous surgical implantation, whereby vertebrae are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for delivery of components of surgical system 10 including inserter 12 and interbody implant 100, as described herein, adjacent an area within the patient's body, such as, for example, vertebrae. In some embodiments, a preparation instrument (not shown) can be employed to prepare tissue surfaces of vertebrae, as well as for aspiration and irrigation of a surgical region.

Inserter 12 is connected with interbody implant 100, as described herein, for disposal in an insertion or delivery orientation, as described herein. Handle 32 is initially disposed in the locking orientation, as described herein. Handle 32 is adjustable and rotatable relative to shaft 14 to adjust position of handle 32 and/or inserter 12 for surgical treatment/delivery of interbody implant 100 and/or to maintain position of navigation component 30, relative to sensor array 202 and/or other components of navigation system 200 to accommodate operating room setup. Inserter 12 includes a four position handle 32 configuration that provides adjustability of hand orientation relative to the patient for ergonomic placement of interbody implant 100. Inserter 12 is adjusted by the practitioner taking into account various factors, such as, for example, patient positioning, a pathway for implant insertion and location of the components navigation system 200, such as, for example, sensor array 202 for initial and operating room setup for surgery. Button 70 is actuated for active unlocking of actuator 68 to overcome the force applied by spring 74 to release handle 32, as described herein. Upon selective positioning of handle 32 relative to shaft 14, button 70 is released for passive locking of handle 32 relative to shaft 14 in the selected position. Interbody implant 100 is disposed adjacent the surgical site.

During the surgery, the practitioner may reposition himself and/or inserter 12 relative to the patient and/or navigation system 200. As such, button 70 is actuated for active unlocking of actuator 68 to release handle 32 for repositioning of handle 32 relative to shaft 14, as described herein. Rotation of handle 32 facilitates adjustment of the position of inserter 12 to allow movement of the practitioner from one side of a surgical table to another side of the surgical table while maintaining a position of navigation component 30 relative to sensor array 202.

Inserter 12 is manipulated to deliver interbody implant 100 to the vertebral space between vertebrae. Sensor array 202 receives signals from navigation component 30 to provide a three-dimensional spatial position and/or a trajectory of inserter 12 and/or interbody implant 100 relative to the vertebral space between vertebrae and/or a depth of inserter 12 and/or interbody implant 100 within the vertebral space for display on monitor 222. Inserter 12 is disengageable from interbody implant 100. In some embodiments, interbody implant 100 provides height restoration between vertebral bodies, decompression, restoration of sagittal and/or coronal balance and/or resistance of subsidence into vertebral endplates.

In some embodiments, the handle/surgical instrument configuration employed in connection with surgical system 10, as described herein, may include and/or be connected with various instruments including the configuration of the present disclosure, such as, for example, inserters, extenders, reducers, spreaders, distractors, blades, retractors, clamps, forceps, elevators and drills, which may be alternately sized and dimensioned, and arranged as a kit.

In some embodiments, surgical system 10 includes an agent, which may be disposed, packed or layered within, on or about the components and/or surfaces of surgical system 10. In some embodiments, the agent may include bone growth promoting material, such as, for example, bone graft to enhance fixation with vertebrae V. The components of surgical system 10 can be made of radiolucent materials such as polymers. Radiomarkers may be included for identification under x-ray, fluoroscopy, CT or other imaging techniques. In some embodiments, the agent may include one or a plurality of therapeutic agents and/or pharmacological agents for release, including sustained release, to treat, for example, pain, inflammation and degeneration. Upon completion of the procedure, the surgical instruments, assemblies and non-implanted components of surgical system 10 are removed from the surgical site and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a member extending along a longitudinal axis between opposite first and second ends, the first end being connectable with a spinal implant;
   a handle coupled to the second end such that the handle is disposed transverse relative to the axis and is rotatable about the axis;
   an actuator disposed in the handle, the actuator including a pin; and
   an inner shaft including a body extending from the second end, the body comprising a surface defining a groove, the inner shaft including a collar, the collar comprising spaced apart slots,
   wherein the actuator is configured to linearly translate the pin toward the first end in a first direction to move the surgical instrument to a non-locking orientation in which the pin is positioned within the groove and the handle is rotatable relative to the member and toward the second end in an opposite second direction to move the surgical instrument to a locked orientation in which the pin is positioned one of the slots and the handle is prevented from rotating relative to the member.

2. A surgical instrument as recited in claim 1, wherein the actuator is resiliently biased to the locked orientation.

3. A surgical instrument as recited in claim 1, wherein the actuator comprises a passive lock in the locked orientation.

4. A surgical instrument as recited in claim 1, wherein the actuator comprises an active lock for disposal in the non-locking orientation.

5. A surgical instrument as recited in claim 1, wherein the slots are circumferentially disposed about the collar and the groove is circumferentially disposed about the body.

6. A surgical instrument as recited in claim 1, wherein the handle is lockable in a plurality of selected positions relative to the member.

7. A surgical instrument as recited in claim 1, wherein the collar comprises opposite first and second end surfaces that each extend perpendicular to the axis, the slots extending through the first end surface without extending through the second end surface.

8. A surgical instrument as recited in claim 1, wherein the surface defines a plurality of slots, the pin being configured to move from the groove and into a respective one the slots defined by the surface and from the respective one of the slots defined by the surface and into one of the slots defined by the collar as the actuator moves from the non-locking orientation to the locking orientation.

9. A surgical instrument as recited in claim 8, wherein:
   the groove is in communication with the slots defined by the surface; and
   the slots defined by the surface are in alignment and communication with the slots defined by the collar.

10. A surgical instrument as recited in claim 1, wherein the actuator comprises a shaft extending parallel to the axis, the pin extending through the shaft of the actuator.

11. A surgical instrument as recited in claim 1, wherein the handle includes a first opening and a second opening that is aligned with the first opening, the actuator comprising a head that extends through the first opening and a shaft that extends through the second opening, the pin extending from the shaft.

12. A surgical instrument as recited in claim 11, wherein the actuator includes a spring disposed about the shaft of the actuator such that the spring is positioned between the head and the pin, the spring biasing the actuator to the locked orientation.

13. A surgical instrument comprising:
- an outer shaft extending along a longitudinal axis between opposite first and second ends, the first end being connectable with a spinal implant;
- a handle coupled to the second end such that the handle is disposed transverse relative to the axis and is rotatable about the axis;
- an actuator connected with the shaft and the handle, the actuator comprising a pin and button; and
- an inner shaft including a body that is coupled to the outer shaft, the body comprising a surface defining a groove, the inner shaft including a collar, the collar comprising spaced apart slots,
- wherein the button is configured to linearly translate the pin toward the first end in a first direction to move the surgical instrument to a non-locking orientation in which the pin is positioned within the groove and the handle is rotatable relative to the member and toward the second end in an opposite second direction to move the surgical instrument to a locked orientation in which the pin is positioned one of the slots and the handle is prevented from rotating relative to the member.

14. A surgical instrument as recited in claim 13, wherein the actuator comprises a passive lock in the locked orientation and is engageable for disposal in the non-locking orientation.

15. A surgical instrument as recited in claim 13, wherein the button is biased to the locked orientation.

16. A surgical instrument as recited in claim 13, wherein the slots are spaced apart and circumferentially disposed about the collar and the groove is circumferentially disposed about the body.

17. A surgical system comprising:
- an interbody implant;
- a surgical instrument connectable with the interbody implant, the surgical instrument including a member defining extending along a longitudinal axis between opposite first and second ends,
- a handle coupled to the second end such that the handle is disposed transverse relative to the axis and is rotatable about the axis,
- an actuator disposed in a cavity of the handle, the actuator being connected with the member and including a pin, and
- an inner shaft including a body extending from the second end, the body comprising a surface defining a groove, the inner shaft including a collar, the collar comprising spaced apart slots,
- wherein the actuator is configured to linearly translate the pin toward the first end in a first direction to move the surgical instrument to a non-locking orientation in which the pin is positioned within the groove and the handle is rotatable relative to the member and toward the second end in an opposite second direction to move the surgical instrument to a locked orientation in which the pin is positioned one of the slots and the handle is prevented from rotating relative to the member.

18. A surgical system as recited in claim 17, wherein the interbody implant is expandable.

* * * * *